(12) United States Patent
Baba

(10) Patent No.: US 7,641,617 B2
(45) Date of Patent: Jan. 5, 2010

(54) WRIST BLOOD PRESSURE GAUGE

(75) Inventor: Toshiaki Baba, Shibukawa (JP)

(73) Assignee: Japan Precision Instruments Inc., Shibukawa-shi (JP)

( * ) Notice: Subject to any disclaimer, the term of this patent is extended or adjusted under 35 U.S.C. 154(b) by 10 days.

(21) Appl. No.: 11/802,559

(22) Filed: May 23, 2007

(65) Prior Publication Data
US 2007/0276266 A1 Nov. 29, 2007

(30) Foreign Application Priority Data
May 25, 2006 (JP) ............................. 2006-004001

(51) Int. Cl.
*A61B 5/02* (2006.01)
(52) U.S. Cl. ..................... 600/503; 600/500; 600/502
(58) Field of Classification Search ................ 600/485, 600/490–504, 26; 359/463; 40/454; 156/64
See application file for complete search history.

(56) References Cited

U.S. PATENT DOCUMENTS

| | | | |
|---|---|---|---|
| 2,815,310 A * | 12/1957 | Anderson | 156/64 |
| 5,724,758 A | 3/1998 | Gulick, Jr. | |
| 5,778,879 A * | 7/1998 | Ota et al. | 600/485 |
| 6,102,846 A * | 8/2000 | Patton et al. | 600/26 |
| 6,385,882 B1 * | 5/2002 | Conley et al. | 40/454 |
| 6,712,769 B2 * | 3/2004 | Freund et al. | 600/503 |
| 7,101,338 B2 * | 9/2006 | Yang | 600/485 |
| 2004/0077958 A1 * | 4/2004 | Kato et al. | 600/490 |
| 2004/0263969 A1 * | 12/2004 | Lipton et al. | 359/463 |
| 2005/0192501 A1 * | 9/2005 | Sano et al. | 600/499 |

FOREIGN PATENT DOCUMENTS

JP 07-289527 11/1995
JP 08-000580 1/1996

OTHER PUBLICATIONS

Extended European Search Report dated Sep. 10, 2007, issued in Application No. EP 07 10 8596.

* cited by examiner

*Primary Examiner*—Robert L Nasser
*Assistant Examiner*—Karen E Toth
(74) *Attorney, Agent, or Firm*—Merek, Blackman & Voorhees; Catherine M. Voorhees (57) ABSTRACT

A convenient, inexpensive wrist blood pressure gauge whereby a cuff can easily be adjusted to the height of the heart merely by adding a simple structure. A lenticular sheet (display body (14)) whose visible image varies according to an angle in relation to a sight line (S) of a measurement subject is provided to a wrist blood pressure gauge (1) worn on a wrist (Mt) of the measurement subject (M), wherein a specific image is visible to the eyes (Ma) of the measurement subject when the wrist is set at the correct height in relation to the heart (H), and a different image is visible to the eyes of the measurement subject when the wrist is not in an appropriate height range.

5 Claims, 7 Drawing Sheets

WRIST BLOOD PRESSURE GAUGE

BACKGROUND OF THE INVENTION

1. Field of the Invention

The present invention relates to a wrist blood pressure gauge that provides a way for a cuff worn on the wrist during blood pressure measurement to be adjusted to the height of the heart.

2. Description of the Related Art

Although not an issue when measuring blood pressure in the upper arm, when blood pressure is measured in the wrist, the height of the wrist in which the blood pressure is being measured must be substantially the same as the height of the heart. The reason for this is that the measurement results are affected by the water head pressure difference when the wrist and heart are at different heights, and an accurate measurement cannot be obtained.

Conventionally, when blood pressure is measured using this type of wrist blood pressure gauge in the past, the cuff is first placed on the wrist, after which the elbow is placed on a table, for example, the forearm is gradually raised until the height of the cuff is visually confirmed to be even with the height of the heart, and blood pressure measurement is started in this position.

However, when the heights are matched visually, the height can be uneven in each measurement, and there is a risk of fluctuation in the measured value.

In order to overcome these drawbacks, the wrist blood pressure gauge has been proposed in Japanese Patent Application Laid-Open Nos. 7-289527 and 8-580, in which a device for detecting a tilt angle is provided to the cuff, and the bend angle of the elbow is detected by the detection device, whereby the height of the wrist is estimated when the elbow is bent.

SUMMARY OF THE INVENTION

However, the tilt detection device provided to the conventional wrist blood pressure gauge described above uses a pendulum principle to detect a tilt, and therefore has a complex structure and high cost.

In view of the foregoing, an object of the present invention is to provide a convenient, inexpensive wrist blood pressure gauge whereby a cuff can easily be adjusted to the height of the heart merely by adding a simple structure.

A first aspect of the present invention is a wrist blood pressure gauge in which a display body whose visible content varies according to an angle in relation to a sight line of a measurement subject is provided to or in a vicinity of a cuff worn on a wrist of the measurement subject, wherein a display of specific content is visible to the measurement subject viewing the display body when the cuff worn on the wrist is set in an appropriate height range in relation to the measurement subject's heart; and a display of content other than the specific content is visible to the measurement subject when the cuff is not in an appropriate height range.

A second aspect of the present invention is the wrist blood pressure gauge according to the first aspect, wherein a lenticular sheet is affixed as the display body to the cuff or to a member in a vicinity of the cuff.

A third aspect of the present invention is the wrist blood pressure gauge according to the second aspect, wherein the lenticular sheet presents a different image according to a difference in an angle with respect to a sight line of a measurement subject between a state in which the cuff is in an appropriate height range and a state in which the cuff is not in an appropriate height range.

A fourth aspect of the present invention Is the wrist blood pressure gauge according to the third aspect, wherein the image comprises text.

A fifth aspect of the present invention is the wrist blood pressure gauge according to the second aspect, wherein the lenticular sheet presents a different color according to a difference in an angle with respect to a sight line of a measurement subject between a state in which the cuff is in an appropriate height range and a state in which the cuff is not in an appropriate height range.

A sixth aspect of the present invention is the wrist blood pressure gauge according to the first aspect, wherein a viewing-angle adjusting sheet is affixed as the display body to the cuff or to a member in a vicinity of the cuff, and the viewing-angle adjusting sheet switches between presenting and not presenting a background color or an image according to a difference in an angle with respect to a sight line of a measurement subject between a state in which the cuff is in an appropriate height range and a state in which the cuff is not in an appropriate height range.

A seventh aspect of the present Invention is the wrist blood pressure gauge according to the first through sixth aspects, wherein the display body is provided to an external surface of an exterior case of a blood pressure gauge body that is integrally provided to the cuff.

An eighth aspect of the present invention is the wrist blood pressure gauge according to the seventh aspect, wherein the display body is provided to an external surface of the exterior case along with a display unit for displaying blood pressure measurement results.

A ninth aspect of the present invention is the wrist blood pressure gauge according to the first through sixth aspects, wherein an operating button for starting blood pressure measurement is provided on the exterior case of the blood pressure gauge body that is integrally provided to the cuff, and the display body is disposed on a pressing surface of the operating button.

In general, blood pressure is preferably measured every day in a certain posture, and daily variations in blood pressure are difficult to verify when there is variation in posture. Therefore, when blood pressure is measured in the wrist, a correct posture is assumed, for example, by sitting in a chair, placing an elbow on a table in front, extending the forearm straight forward, and then bending the elbow to raise the wrist on which the cuff is worn to the height of the heart. The arm may then be stopped, and measurement initiated. In this case, the angle at which the measurement subject views the display body changes as the elbow is bent to raise the wrist to the height of the heart.

In the present invention, the angle at which the eyes of the measurement subject observe the display when, for example, the measurement subject bends the elbow in a certain posture and extends the arm forward, and then raises the wrist on which the cuff is worn to the height of the heart is designated in advance as the correct angle, and specific content is displayed on the display body when the display Is observed at the correct angle. Specifically, the display "OK" is shown in red characters.

When there is a deviation below or above the correct angle range, since there is a difference in height between the heart and the wrist on which the cuff is worn, the display content visible to the measurement subject at this angle differs from the content shown at the aforementioned correct angle. Specifically, the display "NG" is shown in black characters in contrast with the display of "OK" in red characters.

According to this configuration, since the displayed content changes from the black "NG" to the red "OK" when the wrist height matches the height of the heart, the display of "OK" signals that the wrist height matches the height of the heart. In other words, by bending the elbow while watching the display body until the contents of the display body change to the predetermined specific content, it is possible to confirm that the wrist height matches the height of the heart.

Consequently, according to the present invention, the wrist on which the cuff is worn can easily be brought to the height of the heart, and blood pressure can be measured accurately. Since the height is also matched merely by watching for a change in the displayed content, the present invention is user-friendly. Because a lenticular sheet, a viewing-angle adjusting sheet, or the like, for example, may be used as the display body, the present invention can be implemented at low cost and with extreme ease, and with no increase in weight.

Key To Symbols
  1, 101 wrist blood pressure gauge
  10 blood pressure gauge body
  11 exterior case
  12 display unit
  13 operating button
  14 display body
  14A lenticular sheet
  14B viewing-angle adjusting sheet

DESCRIPTION OF THE PREFERRED EMBODIMENTS

Embodiments of the present invention will be described hereinafter with reference to the accompanying drawings.

Figure 1:
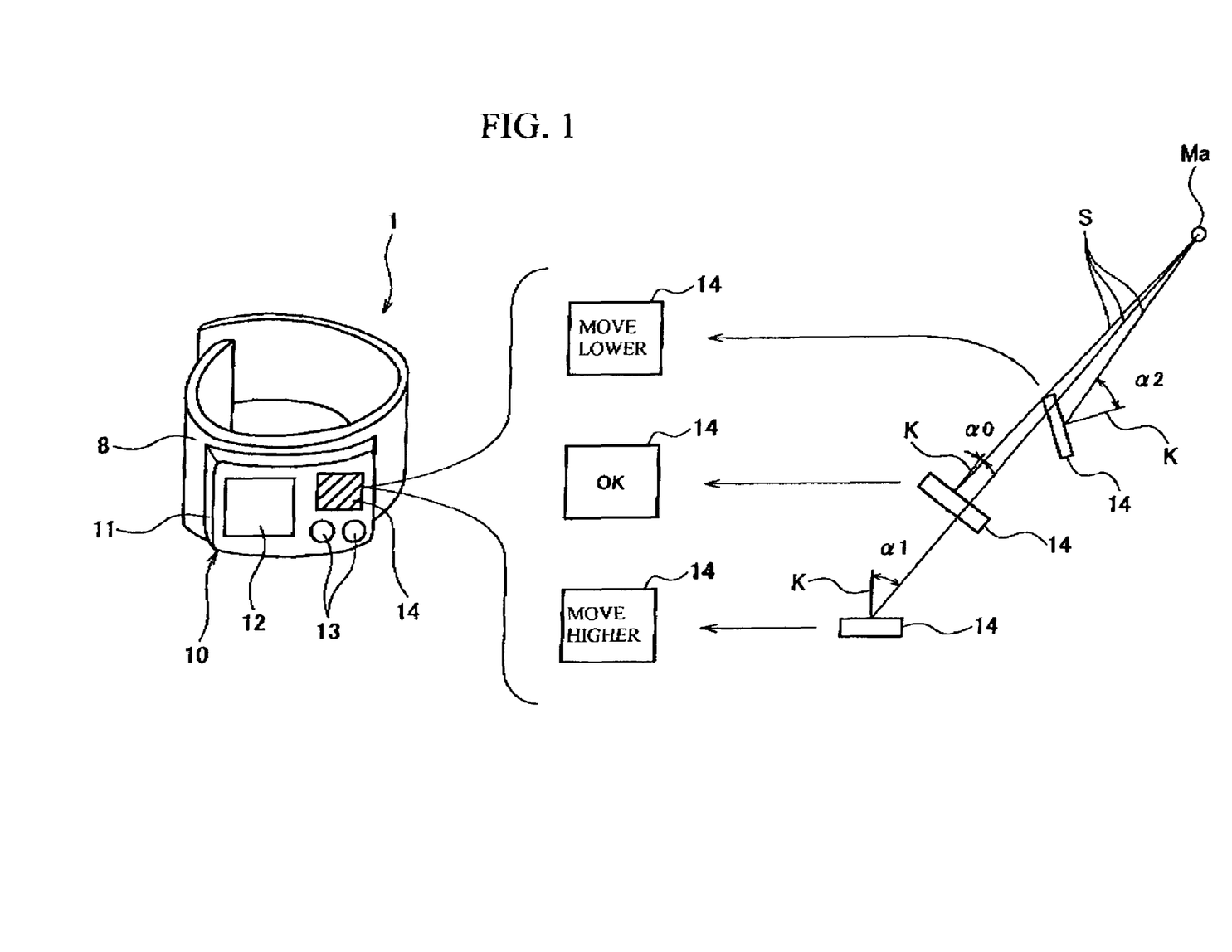
FIG. 1 is a diagram showing the structure of the wrist blood pressure gauge and the content displayed in the display body of the wrist blood pressure gauge according to an embodiment of the present invention.
Figure 2:
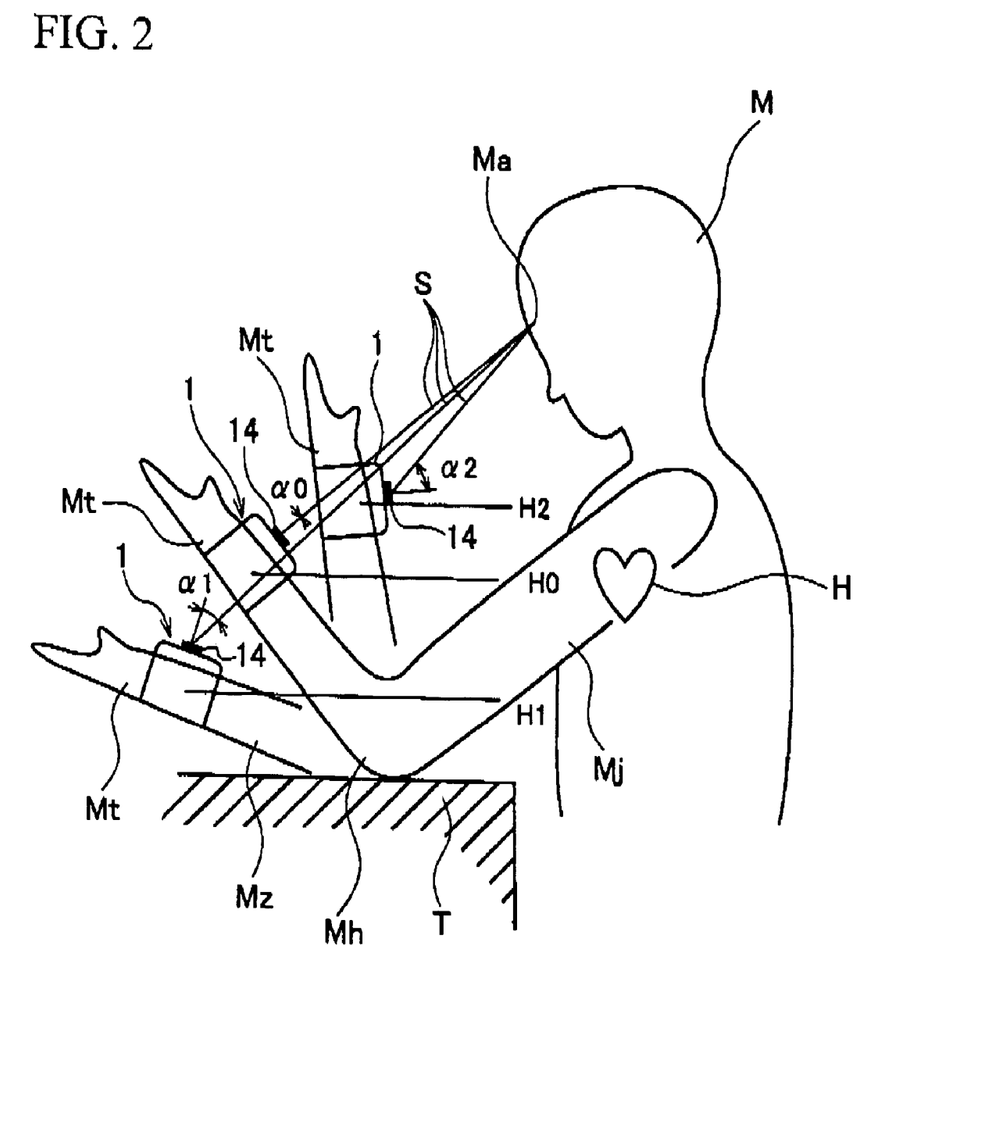
FIG. 2 is a side view showing the same wrist blood pressure gauge in use.

FIG. 1 is a diagram showing the structure of the wrist blood pressure gauge and the content displayed in the display body of the wrist blood pressure gauge according to an embodiment of the present invention; FIG. 2 is a side view showing the same wrist blood pressure gauge in use; and FIG. 3 is an enlarged sectional view showing a lenticular sheet as an example of the display body.

In this wrist blood pressure gauge 1, a blood pressure gauge body 10 is integrally attached to a cuff 8 worn on a wrist Mt of a measurement subject M. Although not shown in the drawings, a pressurizing device for increasing the pressure of the cuff 8, a pressure measurement device for measuring pressure on the basis of a pressure change in the cuff 8, and a control device for performing various types of control are provided inside an exterior case 11 of the blood pressure gauge body 10. A display unit 12 for displaying a measured blood pressure value, and operating buttons 13 as a switch for entering a command for blood pressure measurement are provided to an upper surface of the exterior case 11.

A display body 14 whose content changes according to the angle a0, a1, and a2 with respect to the sight line S of the measurement subject M is provided beside the display unit 12 for the blood pressure measurement results on the upper surface of the exterior case 11. In this configuration, a lenticular sheet 14A such as the one shown in the enlarged sectional view of FIG. 3 is affixed to the surface of the exterior case 11 as a display body 14.

Figure 3:
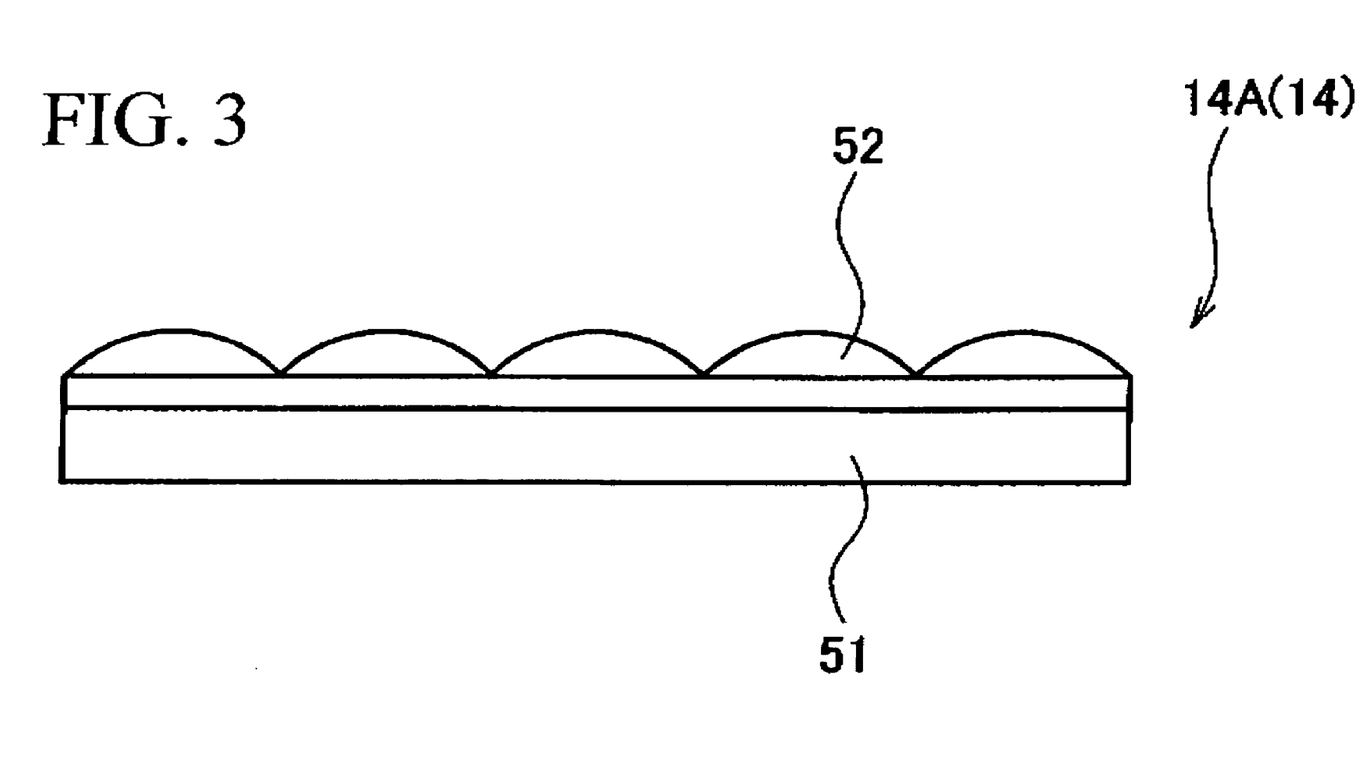
FIG. 3 is an enlarged sectional view showing a lenticular sheet as an example of the display body.

In the lenticular sheet 14A as shown in FIG. 3, lenticular lenses 52 are laminated in an array on the surface of a substrate 51 on which an image (including characters) or other prescribed pattern is printed, and the visible image and color change according to the angle at which the lenticular sheet 14A is viewed.

In this configuration, different displayed content ("OK," "move higher," move lower") is visible according to a change in the angle a0, a1, a2 formed by a reference line (e.g., vertical line) of the display body 14 and the sight line S to the eye Ma of the measurement subject M, for example, as shown in FIG. 1.

In this case, when the measurement subject M has the cuff 8 worn on the wrist Mt set to the appropriate height in relation to the subject's own heart H, the angle of the sight line S to the display body 14 is a0, whereby a specific display content ("OK" in this case) is made visible to the eye Ma of the measurement subject M who is viewing the display body 14. When there is a deviation below or above the correct height range, the angle of the sight line S to the display body 14 is a1 or a2, whereby a display content other than the aforementioned specific content "OK" ("move higher" or "move lower" in this case) is made visible to the eye Ma of the measurement subject M.

The operation of the present invention will next be described.

When blood pressure is measured using the wrist blood pressure gauge 1, the cuff 8 is first placed on the wrist Mt so that the display unit 12 of the blood pressure gauge body 10 is visible in front. With the measurement subject M sitting in a chair or the like, the forearm Mz is then extended in front of the upper arm Mj, and the elbow Mh is rested on the table T, as shown in FIG. 2. In this state, the bending angle of the elbow Mh is reduced to raise the wrist Mt on which the blood pressure gauge 1 is worn to the height of the heart H. The angle of the display body 14 in relation to the sight line S of the measurement subject M then changes, and the content visible on the display varies as the angle changes.

When the display body (lenticular sheet) 14 affixed to the blood pressure gauge body 10 is at substantially the same height H0 as the heart H, the angle of the sight line S to the display body 14 is a0, and a display of "OK" is thus visible. When the display body 14 is at a height H1 that is lower than the heart H, the angle of the sight line S to the display body 14 is a1, and a display of "move higher" is thus visible. When the display body 14 is at a height H2 that is higher than the heart H, the angle of the sight line S to the display body 14 is a2, and a display of "move lower" is thus visible.

Accordingly, by stopping at the height at which "OK" is visible, the wrist Mt can be brought to the same height as the heart H. In other words, it is possible to confirm that the wrist Mt has reached the height of the heart H by watching the display body 14 while flexing the elbow Mh until the content displayed by the display body 14 changes from "move higher" to "OK." When there is too much upward movement, the display "move lower" becomes visible, and the wrist Mt is therefore slightly lowered. Since the display then changes to "OK," stopping the wrist at that point makes it possible to match the height of the wrist Mt to the height of the heart H. A correct blood pressure measurement can thus be performed by starting the measurement with the wrist in the proper position.

In the case of this wrist blood pressure gauge 1, since the height is matched merely by watching for a change in the displayed content of the display body 14, user-friendliness can be demonstrated in the present invention. The lenticular sheet 14A is also used as the display body 14, and the present invention can therefore be easily implemented at extremely low cost, and with no such drawbacks as increased weight.

Any display pattern may be selected for the lenticular sheet 14A. For example, a configuration may be adopted in which a change in the color type, color saturation, or other color change appears, or different images or characters appear according to the viewing angle. Specific examples include a combination of "NG" in red and "NG" in green, a combination of "○" and "×," a combination of types of characters or information, and other displays.

Figure 4:
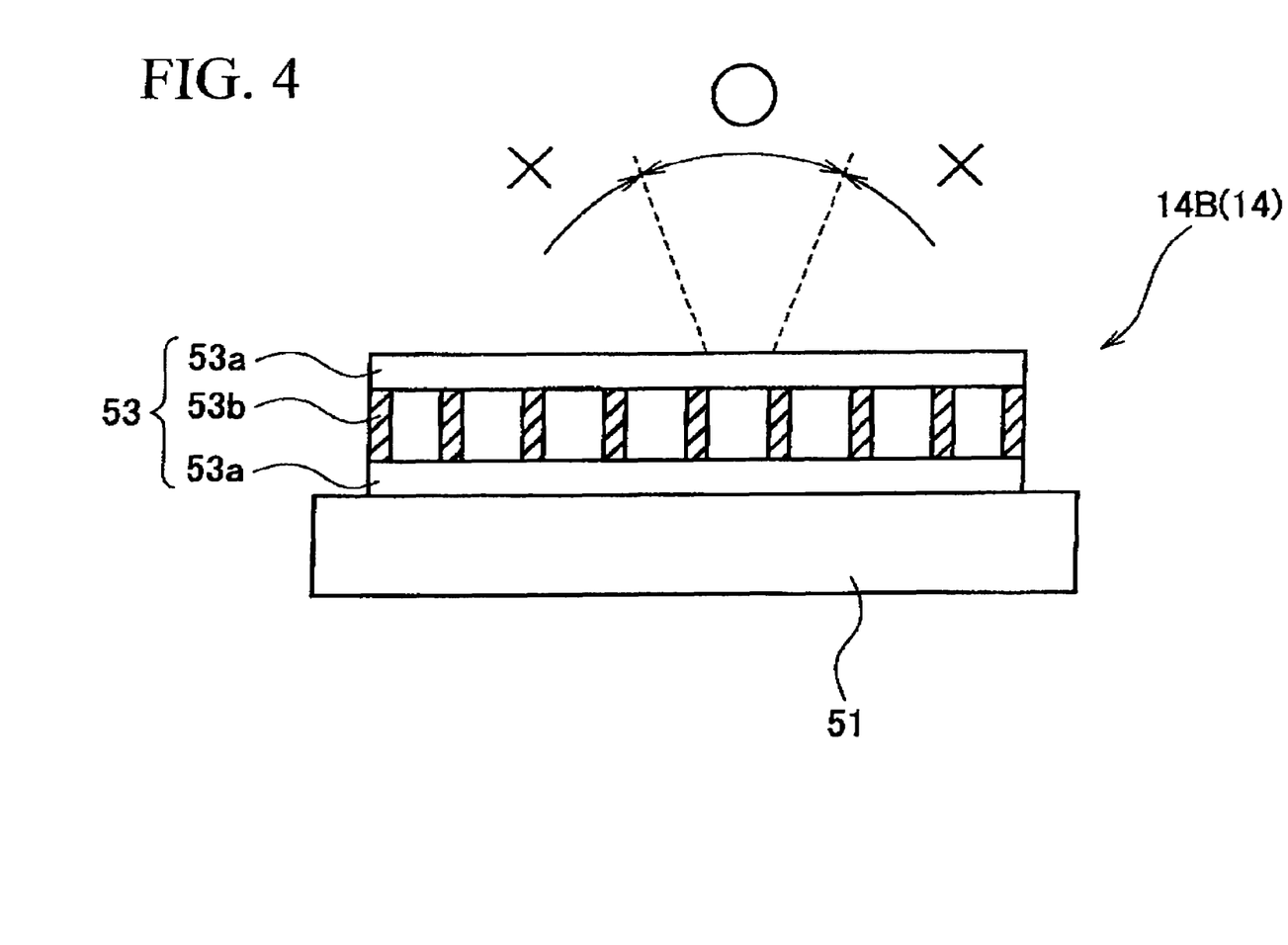
FIG. 4 is an enlarge sectional view showing a viewing-angle adjusting sheet as another example of the display body.

A viewing-angle adjusting sheet 14B such as the one shown in FIG. 4 may also be used as the display body 14. The viewing-angle adjusting sheet 14B is formed by laminating a film 53 in which a louver film 53b is sandwiched between two transparent films 53a on a substrate 51 on which an image is printed. The range of angles at which the image or the like on the substrate 51 is visible is adjusted according to the specifications of the louver film 53b. Accordingly, the background color or the visibility of the image can be switched according to a change in the angle of the display body 14 in relation to the sight line S of the measurement subject when the wrist Mt on which the cuff 8 is worn is inside or outside the correct height range.

Figure 5:
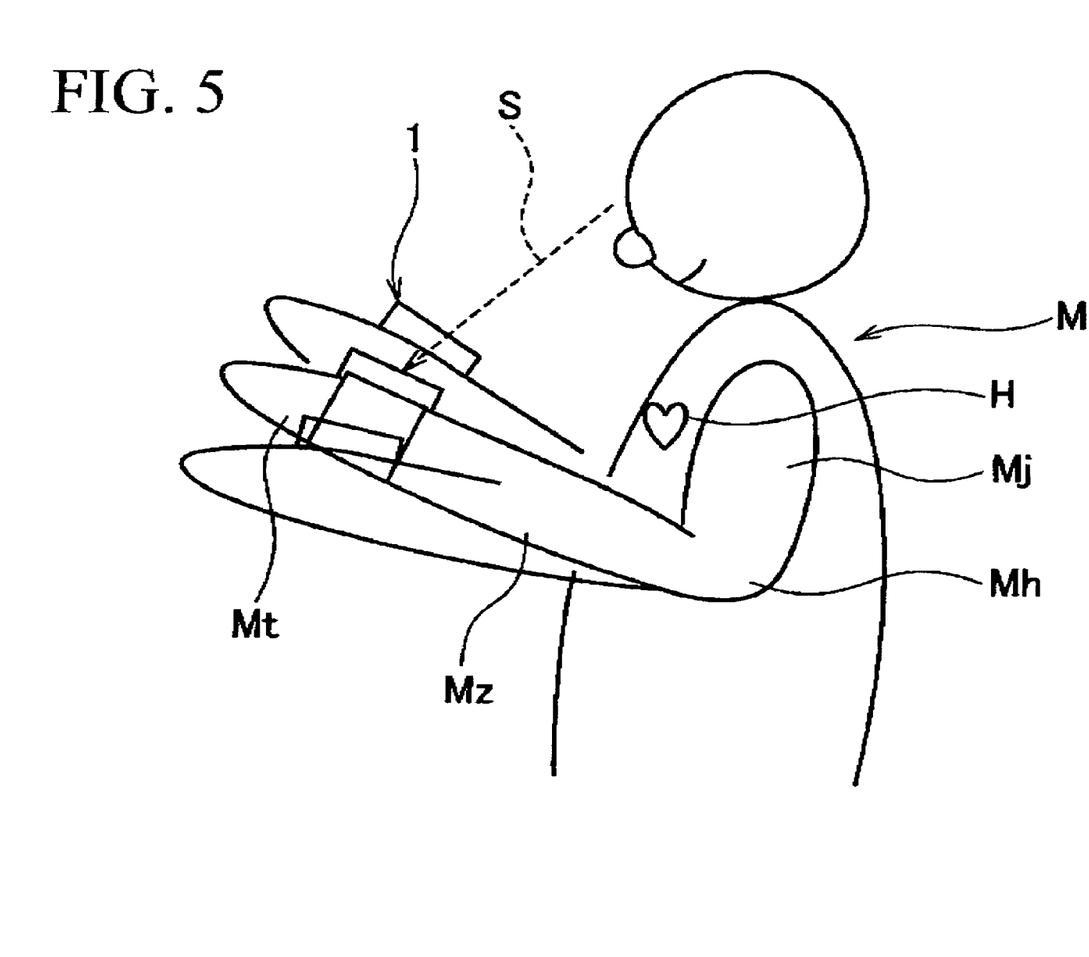
FIG. 5 is a diagram showing another measurement posture.

In the aforementioned embodiment, the angle (angle with respect to the sight line S) at which the display of the display body 14 changes was described in a case in which the elbow Mh was placed on the table T, and the wrist Mt was raised while the elbow Mh was flexed. However, as shown in FIG. 5, the angle at which the display body 14 is visible changes when the wrist Mt is raised while flexing the elbow Mh in a state in which the elbow Mh is against the side of the body. Therefore, when such a measurement posture is recommended, this posture may be assumed in determining the angle at which the display content of the display body 14 changes.

Two types of display bodies that are adapted to two types of measurement postures may also be provided when it is unknown which of the two measurement postures will be assumed.

Figure 6:
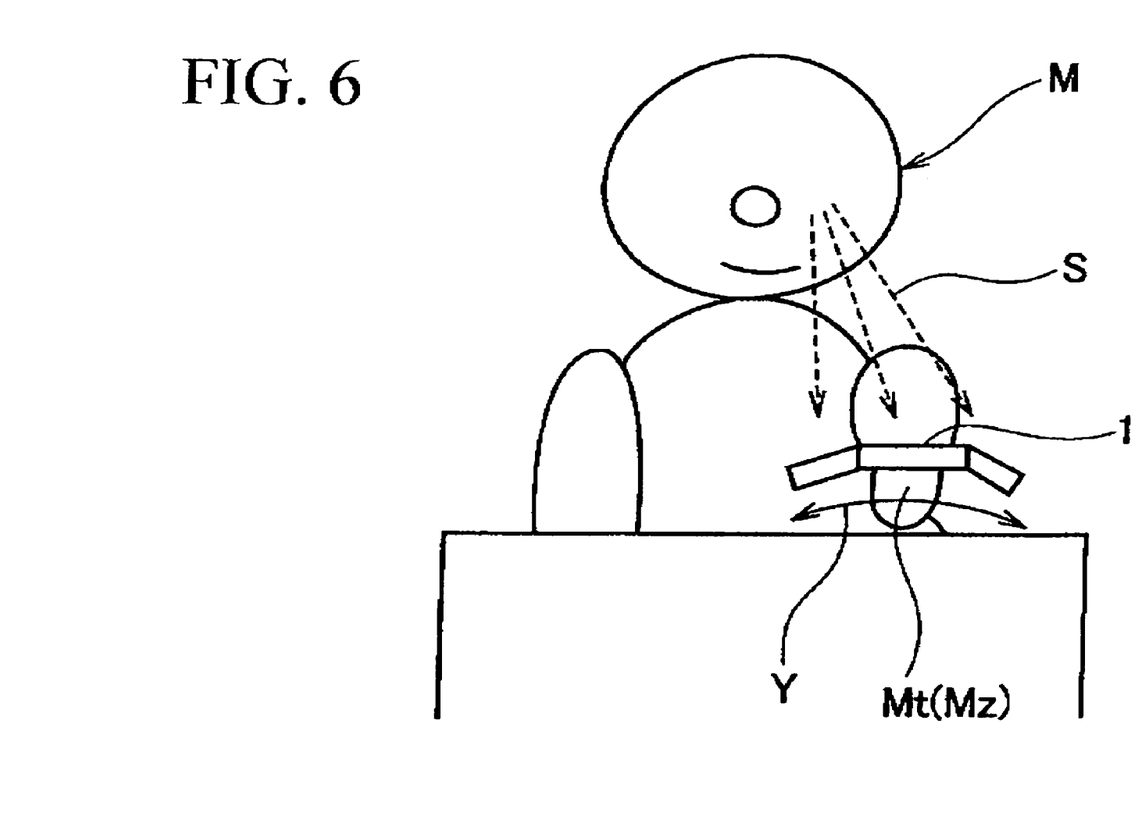
FIG. 6 is a diagram showing a case in which there is twisting of the wrist or forearm.

As shown in FIG. 6, a blood pressure measurement is preferably performed without any twisting of the wrist Mt or forearm Mz to the left or right (the directions indicated by the arrow Y), but some twisting may occur according to the subject. In such cases, the same display body 14 or a separately provided display body of the same type may be used to notify of twisting or induce correction of twisting by changing the visible image.

A case was described in the aforementioned embodiment in which the display body 14 was affixed in a different position from the operating buttons 13, but the display body 14 may be affixed to a pressing surface of one of the operating buttons 13 for starting the blood pressure measurement. In such a case, a correct measurement can be performed by pressing the operating button 13 when a display of "OK," for example, is visible.

Figure 7:
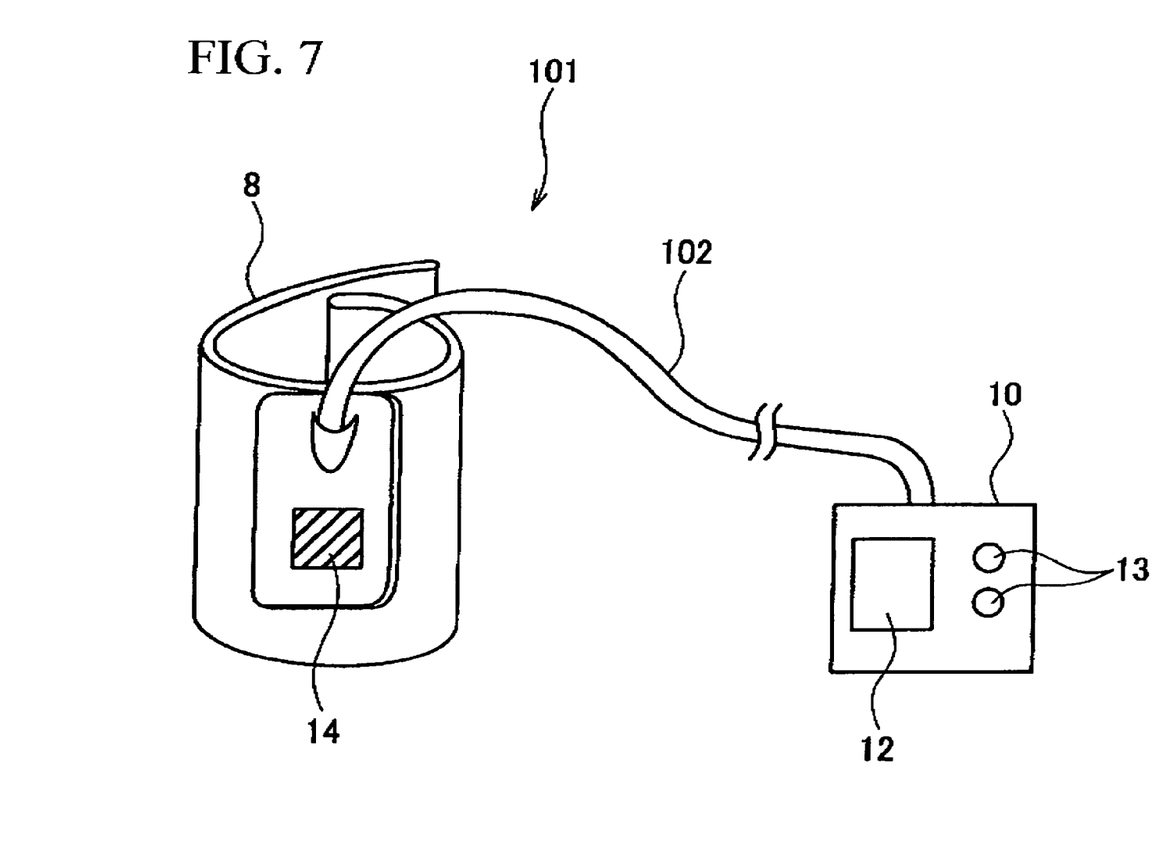
FIG. 7 is a structural diagram showing the wrist blood pressure gauge according to another embodiment.

The display body 14 may be affixed in any location insofar as the location is near the cuff 8 and visible to the measurement subject. For example, in the case of a wrist blood pressure gauge 101 in which the blood pressure gauge body 10 and the cuff 8 are in separate structures as shown in FIG. 7, the display body 14 may be affixed to the cuff 8.

What is claimed is:

1. A wrist blood pressure gauge comprising:
a cuff configured to be worn on a wrist of a measurement subject;
a blood pressure gauge body that calculates a blood pressure value, said gauge body having a display unit for displaying the blood pressure value;
a lenticular sheet whose visible predetermined specific content is displayed corresponding to an angle in relation to a sight line of the measurement subject is provided to or in a vicinity of the cuff worn on a wrist of the measurement subject; and
an operating button for starting blood pressure measurement is provided on an exterior case of the blood pressure gauge body that is integrally provided to said cuff; and
said lenticular sheet is disposed on a pressing surface of the operating button, wherein
the lenticular sheet is an additional structure different from the display unit;
the lenticular sheet of predetermined specific content is visible to the measurement subject viewing the lenticular sheet when said cuff worn on the wrist is set in an appropriate height range in relation to the measurement subject's heart; and
the lenticular sheet displays another previously defined content other than the specific content to the measurement subject when the cuff is not in an appropriate height range.

2. The wrist blood pressure gauge according to claim 1, wherein said lenticular sheet presents a different color according to a difference in an angle with respect to a sight line of a measurement subject between a state in which said cuff is in an appropriate height range and a state in which said cuff is not in an appropriate height range.

3. The wrist blood pressure gauge according to claim 1, wherein said lenticular sheet is affixed in a location near the cuff and visible to the measurement subject.

4. A wrist blood pressure gauge comprising:
a cuff configured to be worn on a wrist of a measurement subject;
a blood pressure gauge body that calculates a blood pressure value, said gauge body having a display unit for displaying the blood pressure value; and
a lenticular sheet whose visible predetermined specific content is displayed corresponding to an angle in relation to a sight line of the measurement subject is provided to or in a vicinity of the cuff worn on a wrist of the measurement subject; and
an operating button for starting blood pressure measurement is provided on an exterior case of the blood pressure gauge body that is integrally provided to said cuff; and
said lenticular sheet is disposed on a pressing surface of the operating button wherein
the lenticular sheet is an additional structure different from the display unit;

the lenticular sheet of predetermined specific content is visible to the measurement subject viewing the lenticular sheet when said cuff worn on the wrist is set in an appropriate height range in relation to the measurement subject's heart;

the lenticular sheet displays another previously defined content other than the specific content to the measurement subject when the cuff is not in an appropriate height range and said lenticular sheet presents a different image according to a difference in an angle with respect to a sight line of measurement subject between a state in which said cuff is in an appropriate height range and a state in which said cuff is not in an appropriate height range.

5. A wrist blood pressure gauge comprising:

a cuff configured to be worn on a wrist of a measurement subject;

a blood pressure gauge body that calculates a blood pressure value, said gauge body having a display unit for displaying the blood pressure value; and a lenticular sheet whose visible predetermined specific content is displayed corresponding to an angle in relation to a sight line of the measurement subject is provided to or in a vicinity of the cuff worn on a wrist of the measurement subject; and an operating button for starting blood pressure measurement is provided on an exterior case of the blood pressure gauge body that is integrally provided to said cuff; and said lenticular sheet is disposed on a pressing surface of the operating button wherein the lenticular sheet is an additional structure different from the display unit;

the lenticular sheet of predetermined specific content is visible to the measurement subject viewing the lenticular sheet when said cuff worn on the wrist is set in an appropriate height range in relation to the measurement subject's heart;

the lenticular sheet displays another previously defined content other than the specific content to the measurement subject when the cuff is not in an appropriate height range; and said lenticular sheet presents a different image according to a difference in an angle with respect to a sight line of measurement subject between a state in which said cuff is in an appropriate height range and a state in which said cuff is not in an appropriate height range where said image comprises text.

* * * * *